United States Patent
Berg

[11] Patent Number: 5,151,160
[45] Date of Patent: Sep. 29, 1992

[54] DEHYDRATION OF 2-METHOXYETHANOL BY EXTRACTIVE DISTILLATION

[75] Inventor: Lloyd Berg, 1314 South Third Ave., Bozeman, Mont. 59715

[73] Assignee: Lloyd Berg, Bozeman, Mont.

[21] Appl. No.: 864,229

[22] Filed: Apr. 6, 1992

[51] Int. Cl.$^5$ .................... B01D 3/40; C07C 41/42
[52] U.S. Cl. .................................. 203/14; 203/18; 203/57; 203/58; 203/60; 203/64; 568/699
[58] Field of Search ............... 203/14, 18, 57, 58, 203/60, 64; 568/699

[56] References Cited

U.S. PATENT DOCUMENTS

| | | | |
|---|---|---|---|
| 3,404,175 | 10/1968 | Mercier | 203/14 |
| 3,625,836 | 12/1971 | Stansbury et al. | 568/699 |
| 4,666,563 | 5/1987 | Berg et al. | 203/14 |
| 4,675,082 | 6/1987 | Gupta | 568/699 |
| 4,943,354 | 7/1990 | Osterburg et al. | 203/14 |

FOREIGN PATENT DOCUMENTS

| | | | |
|---|---|---|---|
| 54-12307 | 1/1979 | Japan | 568/699 |
| 271169 | 5/1927 | United Kingdom | 568/699 |

*Primary Examiner*—Wilbur Bascomb, Jr.

[57] ABSTRACT

2-Methoxyethanol cannot be completely separated from water by conventional distillation or rectification because of the minimum boiling azeotrope. 2-Methoxyethanol can be readily separated from water by extractive distillation. Effective agents are dimethylsulfoxide, sulfolane, dimethylformamide or 1,4-butanediol.

1 Claim, No Drawings

DEHYDRATION OF 2-METHOXYETHANOL BY EXTRACTIVE DISTILLATION

FIELD OF THE INVENTION

This invention relates to a method for the dehydration of 2-methoxyethanol using certain organic compounds as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

2-Methoxyethanol, B.P.=124.5° C. and water, B.P.=100° C. form a minimum boiling azeotrope at 99.9° C. and containing 78% water and thus cannot be separated completely by ordinary distillation or rectification. Extractive distillation would be an attractive method of effecting the separation of water from 2-methoxyethanol if agents can be found that (1) will enhance the relative volatility between water and 2-methoxyethanol and (2) are easy to recover, that is, form no azeotrope with water or 2-methoxyethanol and boil sufficiently above water and 2-methoxyethanol to make separation by rectification possible with only a few theoretical plates.

Extractive distillation typically requires the addition of an equal amount to twice as much extractive agent as the 2-methoxyethanol-water mixture on each plate of the rectification column. The extractive agent should be heated to about the same temperature as the plate into which it is introduced. Thus, extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. I recommend twenty Celcius degrees or higher difference. It is also desirable that the extractive agent be miscible with the 2-methoxyethanol and water otherwise it will form a two phase azeotrope with it and some other method of separation will have to be employed.

TABLE 1

Effect Of Relative Volatility On The Separation Of 2-Methoxyethanol From Water At 99% Purity

| Relative Volatility | Theoretical Plates | Actual Plates 75% Efficiency | Actual Plates, 75% Eff., Min. Reflux |
|---|---|---|---|
| 1.2 | 50 | 67 | 87 |
| 1.5 | 23 | 31 | 40 |
| 2.0 | 13 | 17 | 22 |
| 2.5 | 10 | 13 | 18 |

The advantage of employing an effective extractive distillation agent is shown in Table 1. 2-Methoxyethanol forms a minimum boiling azeotrope with water which possesses a relative volatility of 1.0 and cannot be separated by rectification. If extractive distillation is employed with an agent yielding a relative volatility of 2.5, a rectification column of only eighteen actual plates will be required to produce products of 99% purity.

OBJECTIVE OF THE INVENTION

The objects of this invention are to provide a process or method of extractive distillation that will enhance the relative volatility of 2-methoxyethanol to water in their separation in a rectification column. It is a further object of this invention to identify organic compounds that are stable, can be separated from 2-methoxyethanol by rectification with relatively few plates and can be recycled to the extractive distillation column with little decomposition.

SUMMARY OF THE INVENTION

The objects of this invention are provided by a process for the separation of 2-methoxyethanol from water which entails the use of certain organic compounds as the agent in extractive distillation.

TABLE 2

Effective Agents For Separating 2-Methoxyethanol From Water

| Compounds | Relative Volatility |
|---|---|
| Dimethylsulfoxide | 1.7 |
| Dimethylformamide | 1.6 |
| Dimethylacetamide | 1.8 |
| Sulfolane | 2.0 |
| Ethylene glycol | 1.2 |
| 1,2-Butanediol | 2.3 |
| 1,3-Butanediol | 1.8 |
| 1,4-Butanediol | 1.7 |
| 1,5-Pentanediol | 1.35 |
| Hexylene glycol | 2.5 |
| Dipropylene glycol | 1.8 |
| Diethylene glycol | 1.3 |
| Triethylene glycol | 1.3 |
| Tetraethylene glycol | 1.3 |
| Tripropylene glycol | 2.1 |
| 2-Methyl-1,3-propanediol | 2.1 |
| Polyethylene glycol 200 | 1.35 |

TABLE 3

| Ineffective Agents For Separating 2-Methoxyethanol From Water | |
|---|---|
| Adiponitrile | Propylene glycol |
| Ethanol amine | Formamide |

TABLE 4

| | Data From Run Made In Rectification Column | | | | |
|---|---|---|---|---|---|
| Agent | Column | Time hrs. | Temp. °C. | Wt. % Water | Wt. % 2-MethoxyEtOH | Relative Volatility |
| 1,4-Butanediol | Overhead | 1 | 86 | 99.7 | 0.3 | 1.7 |
| | Bottoms | | 110 | 87.8 | 12.2 | |
| " | Overhead | 2 | 86 | 99.7 | 0.3 | 1.7 |
| | Bottoms | | 115 | 88 | 12 | |

DETAILED DESCRIPTION OF THE INVENTION

I have discovered that certain organic compounds will effectively increase the relative volatility between 2-methoxyethanol and water when employed as the agent in extractive distillation. The data in Table 2 was obtained in a vapor liquid equilbrium still. Table 2 lists the compounds found to be effective extractive distillation agents to separate water from 2-methoxyethanol. They are dimethylsulfoxide, dimethylformamide, dimethylacetamide, sulfolane, ethylene glycol, 1,2-butanediol, 1,3-butanediol, 1,4-butanediol, 1,5-pentanediol, hexylene glycol, dipropylene glycol, diethylene glycol, triethylene glycol, tetraethylene glycol, tripropylene glycol, 2-methyl-1,3-propanediol, and polyethylene glycol 200.

Table 3 lists the compounds that were found to be ineffective agents for separating water from 2-methoxyethanol.

One of the agents, 1,4-butanediol, whose relative volatility had been detremined in the vapor-liquid equilibrium still, was then evaluated in a glass perforated plate rectification column and the results listed in Table 4. 1,4-Butanediol gave a relative volatility 1.7 after one and two hours of continuous operation.

THE USEFULNESS OF THE INVENTION

The usefulness or utility of this invention can be demonstrated by referring to the data presented in Tables 2 and 4. All of the successful agents show that water can be separated from 2-methoxyethanol by means of extractive distillation in a rectification column and that the ease of separation as measured by relative volatility is considerable.

WORKING EXAMPLES

Example 1

Sixty grams of the water-2-methoxyethanol azeotrope and 60 grams of sulfolane were charged to a vapor-liquid equilibrium still and refluxed for three hours. Analysis indicated a vapor composition of 86.8% water, 13.2% 2-methoxyethanol; a liquid composition of 76.5% water, 23.5% 2-methoxyethanol which is a relative volatility of 2.0.

Example 2

Sixty grams of the water-2-methoxyethanol azeotrope and 60 grams of 1,4-butanediol were charged to the vapor-liquid equilibrium still and refluxed for five hours. Analysis indicated a vapor composition of 87.7% water, 12.3% 2-methoxyethanol; a liquid composition of 80.7% water, 19.3% 2-methoxyethanol which is a relative volatility of 1.7.

Example 3

A solution comprising 400 grams of the water-2-methoxyethanol azeotrope was placed in the stillpot of a 7.3 theoretical plate glass perforated plate rectification column. When refluxing began, an extractive agent comprising 1,4-butanediol was pumped into the column at a rate of 15 ml/min. The temperature of the extractive agent as it entered the column was 95° C. After establishing the feed rate of the extractive agent, the heat input to the water-2-methoxyethanol in the stillpot was adjusted to give a total reflux rate of 40 ml/min. After one hour of operation, overhead and bottoms samples were collected and analysed by gas chromatography. The overhead analysis was 99.7% water, 0.3% 2-methoxyethanol and the bottoms analysis was 87.8% water, 12.2% 2-methoxyethanol. This gives an average relative volatility of 1.7 for each theoretical plate. After two hours of operation, samples were again taken and analysed. The overhead analysis was 99.7% water, 0.3% 2-methoxyethanol; the bottoms analysis was 88% water, 12% 2-methoxyethanol which is an average relative volatility of 1.7 for each theoretical plate. These data are presented in Table 4.

I claim:

1. A method for recovering water from a mixture of water and 2-methoxyethanol which comprises distilling a mixture of water and 2-methoxyethanol in the presence of about one part of an extractive agent per part of water-2-methoxyethanol mixture, recovering the water as overhead product and obtaining the 2-methoxyethanol and the extractive agent from the stillpot, wherein said extractive agent consists of one material selected from the group consisting of dimethylsulfoxide, dimethylformamide, dimethylacetamide, sulfolane, ethylene glycol, 1,2-butanediol, 1,3-butanediol, 1,4-butanediol, 1,5-pentanediol, hexylene glycol, dipropylene glycol, diethylene glycol, triethylene glycol, tetraethylene glycol, tripropylene glycol, 2-methyl-1,3-propanediol and polyethylene glycol 200.

* * * * *